United States Patent [19]

Harrison et al.

[11] Patent Number: 5,599,692
[45] Date of Patent: *Feb. 4, 1997

[54] ANTIGENIC POLYPEPTIDES OF *TAENIA OVIS*

[75] Inventors: Gavin B. L. Harrison; Robert P. Dempster, both of Upper Hutt, New Zealand; Michael D. Rickard, Werribee, Australia; Marshall W. Lightowlers, Williamstown, Australia; Kim L. O'Hoy, Melbourne, Australia; Kevin S. Johnson, Godmanchester, United Kingdom; David D. Heath; Stephen B. Lawrence, both of Upper Hutt, New Zealand; Jennifer G. Vinton, Lower Hutt, New Zealand

[73] Assignees: Coopers Animal Health NZ Limited, Upper Hutt, New Zealand; University of Melbourne, Victoria, Australia; Ministry of Agriculture & Fisheries, Wellington, New Zealand

[*] Notice: The portion of the term of this patent subsequent to Mar. 9, 2010, has been disclaimed.

[21] Appl. No.: 393,383

[22] Filed: Feb. 23, 1995

Related U.S. Application Data

[62] Division of Ser. No. 268,535, Jul. 6, 1994, which is a division of Ser. No. 851,112, Mar. 16, 1992, Pat. No. 5,348,740, which is a continuation of Ser. No. 349,723, May 9, 1989, abandoned.

[30] Foreign Application Priority Data

May 12, 1988 [NZ] New Zealand ............................ 224597
Jun. 1, 1988 [NZ] New Zealand ............................ 224862

[51] Int. Cl.$^6$ ................ C12N 15/12; C07K 14/435; A61K 39/00
[52] U.S. Cl. ............ 435/69.3; 424/185.1; 424/266.1; 435/252.3; 435/252.33; 435/320.1; 530/350; 530/387.1; 530/395; 536/23.5

[58] Field of Search ............... 536/23.5; 530/387.1, 530/388.2, 388.6, 395, 387.9; 435/69.3, 252.3

[56] References Cited

U.S. PATENT DOCUMENTS 5,366,728  11/1994  Harrison et al. .................... 424/191.1

FOREIGN PATENT DOCUMENTS

WO88/01277  of 1988  WIPO .

OTHER PUBLICATIONS

J. Mol. Biochem. Parasitol, 1988, 28 (1988), pp. 21–30.
Nature, 1989, 338 (621), pp. 585–587.
Adv. Parasitology, 21, (1982), pp. 230–296.
Howell, M. J. et al. "Cloning and expression of *T. ovis* . . . " Mol. Biochem. Parasitol, 28, pp. 21–30.
Craig, P. S. et al. "Antibody responses . . . " Z. Parasitol, 67 (2), pp. 197–209.
Osborn, P. J. et al. "Vaccination of . . . " Res. Vet. Sci. 32 (3) 1982) (Abstract only), pp. 350–353.

*Primary Examiner*—Thomas M. Cunningham
*Attorney, Agent, or Firm*—Nixon & Vanderhye

[57] ABSTRACT

This invention relates to polypeptide antigens of *T.ovis* suitable for use in vaccines to protect ruminants against infection by cestode parasites. The antigens are preferably obtained by expression of DNA coding therefor in a recombinant host cell. Aspects of the invention include DNA encoding the antigens, vectors containing the DNA and hosts which express the antigens.

The invention also provides antibody and DNA probes for use in identifying protective antigens of cestode parasites other than *T.ovis*.

19 Claims, 3 Drawing Sheets

Figure 1

Immunoblot analysis of T. ovis oncosphere antigens.

Lane 1  Pharmacia Low Molecular Weight marker kit proteins stained with Aurodye (Janssen).

Lane 2  T. ovis oncosphere antigens probed with Rabbit anti-oncosphere serum

Lane 3  Oncosphere antigens probed with affinity purified antibodies used to select clone 45W.

Lane 4  Oncosphere antigens probed with serum from sheep vaccinated with GST 45W fusion protein

Figure 2

```
        EcoRI
        ------
  1    GAATTC CCG GAC TAC GAA CAA CCC ATC GAG AGA ACA GTG GTA GAA
              Pro Asp Tyr Glu Gln Pro Ile Glu Arg Thr Val Val Glu    13

46    TAT CCA TCA CTA CGT GAC ATC TTT GCT TGG GAA CCT CCG ACT TCT
       Tyr Pro Ser Leu Arg Asp Ile Phe Ala Trp Glu Pro Pro Thr Ser   28

91    AAC TCC ATT GGC CTA ACT TGG CAA AGG CAT GCA TTT CCT GGT GTG
       Asn Ser Ile Gly Leu Thr Trp Gln Arg His Ala Phe Pro Gly Val   43

136    GAA CGT GAA GTG CTC ACA TTG AAG GCA GTG CCG ACT TCT GAA CCC
       Glu Arg Glu Val Leu Thr Leu Lys Ala Val Pro Thr Ser Glu Pro   58

181    AAT AAC ACC AAG ACA GCA TAT GCA AAG CTC GGC AGC GGA AAA GTC
       Asn Asn Thr Lys Thr Ala Tyr Ala Lys Leu Gly Ser Gly Lys Val   73

226    ACT CTT GAT GGA CTG AAG CCC AAT GCC ACA TAT CTT GTG ACT GCG
       Thr Leu Asp Gly Leu Lys Pro Asn Ala Thr Tyr Leu Val Thr Ala   88

271    ACG GCA AAT ATA AGT GGA GAC ACA ATT CTG GTA TTG AGC AAT ACT
       Thr Ala Asn Ile Ser Gly Asp Thr Ile Leu Val Leu Ser Asn Thr  103

316    TTT CAT ACA CTG GCC AAT GGC ACA AAT ATT ATA AAT AAC ATC TTC
       Phe His Thr Leu Ala Asn Gly Thr Asn Ile Ile Asn Asn Ile Phe  118

361    CAT TGG GGT CCT GTG ACT AAT CAA TCA ATT CAA GTA AGA TGG GAT
       His Trp Gly Pro Val Thr Asn Gln Ser Ile Gln Val Arg Trp Asp  133

406    CAG ATA AAA CCG GAG GAA ACA AGC GCT CTG ATA GTC ACA CTG ACG
       Gln Ile Lys Pro Glu Glu Thr Ser Ala Leu Ile Val Thr Leu Thr  148

451    GCA GAG ATG GCT TCT GAC CCC GGA GTG GAA AGA TCG GAG TCT GCA
       Ala Glu Met Ala Ser Asp Pro Gly Val Glu Arg Ser Glu Ser Ala  163

496    CTC TTC GGT AAA GGA AAG GTC ACT GTT GAC GGA CTG GAG TCC GAC
       Leu Phe Gly Lys Gly Lys Val Thr Val Asp Gly Leu Glu Ser Asp  178

541    ACA CTA TAT ATT GCG ACT GTG ATG GTA TTT AGA AAT GGA AGG CAA
       Thr Leu Tyr Ile Ala Thr Val Met Val Phe Arg Asn Gly Arg Gln  193

586    TAC TTC AAT TCC ACC AGA GAT ATT CGA ACA CTC AAA TCT GGC CAT
       Tyr Phe Asn Ser Thr Arg Asp Ile Arg Thr Leu Lys Ser Gly His  208

631    AAG GAG GTA ACA GTC GTA ACA ACT AGT GGA TCT GGT ATA GCC TCC
       Lys Glu Val Thr Val Val Thr Thr Ser Gly Ser Gly Ile Ala Ser  223

676    ACA ATA CTT GGA CTC CTC CTC ACC TGC GTG GCG CTA GTC CTT GCT
       Thr Ile Leu Gly Leu Leu Leu Thr Cys Val Ala Leu Val Leu Ala  238

721    TGAACACTTGCGTCGGTCAATGCCCATTTCCAAACCATCCATCTTCATCCAATCTCACG
       ---
779    TCCCATGACTTGCTTGTCTGCACCACCTCTTTCTACCTTGCACGCACTCATGGTGTCGC

839    GAGTGCCCCTCTCCCTACTCATTCTTGCTCAACTAATATTGGCTTGACACCTCTTGATG

898    GATAACCACTGAATGGCAAATAAACGAATTC
                            ------
                            EcoRI
```

Figure 3

Autoradiograph of GST fusion proteins reacted with the monoclonal antibody 3F10F6

LANE 1 : GST 45W (BamHI/HincII)

LANE 2 : GST 45W (BamHI/XhoII)

LANE 3 : GST - 45W

LANE 4 : GST - 45S

LANE 5 : GST

ANTIGENIC POLYPEPTIDES OF *TAENIA OVIS*

This is a Rule 60 Divisional of application Ser. No. 08/268,535, filed 6 Jul. 1994, which is Rule 60 Division of application Ser. No. 07/851,112, filed 16 Mar. 1992, now U.S. Pat. No. 5,348,740, which is a continuation of application Ser. No. 07/349,723, filed 9 May 1989, now abandoned.

BACKGROUND OF THE INVENTION

The *Taenia ovis* tapeworm exists in adult form in the small intestine of its primary host, the dog. The cystic stage is carried in the musculature of its secondary or intermediate hosts, notably sheep and goats. Current control measures include prevention of feeding of infected carcases to dogs and treatment of dogs with cestocidal drugs, notably praziquantel (Droncit, Bayer) to prevent transmission of the parasite to ruminants. These control measures are costly to implement and are not effective in eradicating *T.ovis*.

Accordingly, as an adjunct to current control measures and to effect eradication of the disease, it would be preferable to immunise the secondary hosts to protect them from infection and also to preserve carcase quality for the meat industry.

It is an object of the present invention to provide a protective antigen for use in vaccines for the protection of ruminants against *T.ovis* infection or at least to provide the public with a useful choice.

Previous investigations conducted into vaccination against *T.ovis* infection with oncosphere antigens are reviewed by Rickard, M. D and Williams, J. F. Hydatidosis/Cystercercosis: Immune mechanisms and Immunisation against infection, *Adv Parasitology* 21, 230–296 (1982). However, in the work reviewed no attempt was made to identify which antigenic component of the oncospheres was responsible for the immune response. As will be appreciated. *T.ovis* contains a large number of antigenic components, most of which are not immunologically effective against infection.

Earlier attempts have been made to identify a host protective antigen for *T.ovis* (Howell, M. J & Hargreaves, J *J Mol Biochem Parasitol* 28, 21–30 (1988)). A cDNA library was prepared using mRNA extracted from adult *T.ovis* tape worms. Recombinants expressing antigenic determinants as -galactosidase fusion proteins were selected using antibodies in serum from sheep infected with *T.ovis*. Some fusion proteins were shown to correspond with native antigens (92.5 to 180kD) present in adult and oncosphere states of *T.ovis*, but trials of the host-protective nature of purified fusion proteins were not reported.

SUMMARY OF INVENTION

In contrast to the investigations above, the applicants have now identified a 47–52 kD antigenic component of *T.ovis* which acts as an epitope to induce protective immunity in a ruminant to *T.ovis* infection. It is broadly to this antigen, to the methods and means of producing the antigen and to the use of the antigen that the present invention is directed.

Accordingly, in one aspect the present invention may broadly be said to consist in a purified antigenic polypeptide of *T.ovis*

(a) which has a molecular weight in the range of 47–52 kD calculated by SDS-PAGE; and (b) which is capable of generating a protective immunological response to *T.ovis* in a ruminant or an immunologically active fragment thereof.

Preferably, the antigenic polypeptide includes the amino acid sequence set out in FIG. 2.

Conveniently, the protective antigen of the invention is obtained by expression of the DNA sequence coding therefor in a host cell or organism.

In a further aspect, the invention consists in an antigenic polypeptide of *T.ovis* which is capable of generating a protective immunological response to *T.ovis* in a ruminant, which polypeptide includes the amino acid sequence encoded by the DNA sequence of FIG. 2 herein; or an immunologically active fragment of said polypeptide.

In still a further aspect, the invention consists in a composition of matter capable of generating a protective immunological response to *T.ovis* infection in a ruminant which essentially consists of:

(a) a polypeptide having the amino acid sequence of FIG. 2;

(b) an immunologically active fragment of the polypeptide (a); or (c) a variant of (a) or (b) which has been modified by the insertion, substitution or deletion of one or more amino acids and which has equivalent immunological activity thereto.

In still a further aspect, the invention consists in a vaccine which includes an immunogenic polypeptide or fragment thereof as defined above in combination with a pharmaceutically acceptable carrier and/or adjuvant therefor.

In still a further aspect, the invention may be said to consist in a method of protecting a ruminant against infection by a cestode parasite comprising administering to said ruminant an immunologically effective amount of:

(a) a polypeptide or fragment as defined above;

(b) a composition as defined above; or (c) a vaccine as defined above.

In additional aspects, the invention relates to a DNA isolate which comprises a DNA sequence encoding the immunologically effective antigenic polypeptides of the invention; to transformed hosts capable of expressing the antigenic polypeptides encoded: and to methods of producing the antigenic polypeptides comprising culturing the said transformed hosts.

BRIEF DESCRIPTION OF THE DRAWINGS

Although the invention is broadly as described above, it will be appreciated by those persons skilled in the art that the invention is not limited to the foregoing but also includes embodiments of which the following gives examples. In particular, certain aspects of the invention will be more clearly understood by having reference to the accompanying drawings wherein.

FIG. 2 represents the nucleotide sequence of *T. ovis* 45W cDNA and the predicted amino acid sequence of the polypeptide encoded.

DETAILED DESCRIPTION OF THE INVENTION

Previous investigations by the inventors have identified a 47–52 kD molecular weight fraction of the antigenic complement of *T.ovis* as a major antigen to which antibodies were present in immune sheep. These investigations involved the identification of the various antigen fractions of the antigenic complement of *T.ovis* oncospheres through the use of polyacrylamide gel electrophoresis in the presence of sodium dodecyl sulphate (SDS-PAGE) and immunoblotting techniques adapted from the method of Towbin et al (*Proc. Natl. Acad Sci U.S.A.* 76 4350–54 (1979)) and reviewed by Beisiegel (*Electrophoresis,* Volume 7, 1–18 (1986)). Initial experiments using partially purified sources of the major antigen fractions indicated that a significant degree of immunity was induced to *T.ovis* infection by one of these fractions. The molecular weight of the subject antigen was calculated as between 47–52 kD from the immunoblots using Pharmacia molecular weight markers.

The present invention therefore has as its first aspect an antigenic polypeptide of *T.ovis* having a molecular weight in the range of 47–52 kD as determined by SDS-PAGE and which is capable of generating a protective immunological response to *T.ovis*. The invention also specifically contemplates immunologically active fragments of such a polypeptide.

In a preferred form of this aspect of the invention, there are provided immunologically active fragments of the polypeptide, the fragments comprising at least amino acids 1–172 of the sequence of FIG. 2, more preferably amino acids 1–217 of the sequence of FIG. 2, most preferably the entire amino acid sequence of FIG. 2. It will however be appreciated that modifications can be made to the native sequence of both the polypeptide and its active fragments whilst at least substantially retaining their biological activity. Such modifications to the native amino acid sequence to result in the insertion, substitution or deletion of one or more amino acids are specifically within the scope of this invention.

The antigenic polypeptides and fragments of the invention can be prepared in a variety of ways. For example, they can be produced by isolation from a natural source, by synthesis using any suitable known technique (such as by the stepwise solid phase approach described by Merrifield (1962) *J. Amer Chem. Soc* 85 2149–2156) or, as is preferred, through employing recombinant DNA techniques.

The variants of both the native polypeptide and its active fragments can similarly be made by any of those techniques known in the art. For example, variants can be prepared by site-specific mutagenesis of the DNA encoding the native amino acid sequence.

Site-specific mutagenesis allows the production of variants through the use of specific oligonucleotide sequences which encode the DNA sequence of the desired mutation, as well as a sufficient number of adjacent nucleotides, to provide a primer sequence of sufficient size and sequence complexity to form a stable duplex on both sides of the deletion junction being traversed. Typically, a primer of about 20 to 25 nucleotides in length is preferred, with about 5 to 10 residues on both sides of the junction of the sequence being altered. In general, the technique of site-specific mutagenesis is well known in the art as exemplified by publications such as Adelman et al., *DNA* 2, 183 (1983).

In a further aspect, the invention accordingly relates to the recombinant production of the antigenic polypeptides and active fragments defined above.

Stated generally, the production of the protective antigen of the invention by recombinant DNA techniques involves the transformation of a suitable host organism or cell with an expression vector including a DNA sequence coding for the antigen, followed by the culturing of the transformed host and subsequent recovery of the antigen expressed.

An initial step in the method of recombinantly producing the antigen involves the ligation of a DNA sequence encoding the antigen into a suitable expression vector containing a promoter and ribosome binding site operable in the host cell in which the coding sequence will be transformed. The most common examples of such expression vectors are plasmids which are double stranded DNA loops that replicate autonomously in the host cell. However, it will be understood that suitable vectors other than plasmids can be used in performing the invention.

Preferably, the host cell in which the DNA sequence encoding the polypeptide is cloned and expressed is a prokaryote such as *E. coli*. For example, *E. coli* K12 strain 294 (ATCC 31446), *E. coli* B, *E. coli* X1776 (ATCC 31537) *E. coli* strain ST9 or *E. coli* JM 101 can be employed. Other prokaryotes can also be used, for example bacilli such as *Bacillus subtilis* and enterobacteriaceae such as *Salmonella typhimurium* or *Serratia marcesans*.

In general, where the host cell is a prokaryote, expression or cloning vectors containing replication and control sequences which are derived from species compatible with the host cell are used. The vector may also carry marking sequences which are capable of providing phenotypic selection in transformed cells. For example, *E. coli* has commonly been transformed using pBR322, a plasmid derived from an *E. coli* species (Bolivar, et al., *Gene* 2: 95 (1977)). pBR322 contains genes for ampicillin and tetracycline resistance and thus provides easy means for identifying transformed cells.

For use in expression, the plasmid including the DNA to be expressed contains a promoter. Those promoters most commonly used in recombinant DNA construction for use with prokaryotic hosts include the -lactamase (penicillinase) and lactose promoter systems (Chang et al, *Nature,* 275: 615 (1978); Itakura, et al, *Science,* 198: 1056 (1977); Goeddel, et al *Nature* 281: 544 (1979)) and a tryptophan (trp) promoter system (Goeddel, et al, *Nucleic Acids Res.,* 8: 4057 (1980); EPO Publ No. 0036776). While these are the most commonly used, other microbial promoters such as the tac promoter (Amann et al., *Gene* 25, 167–178 (1983)) have been constructed and utilised, and details concerning their nucleotide sequences have been published, enabling a skilled worker to ligate them functionally in operable relationship to genes in vectors (Siebenlist, et al, *Cell* 20: 269 (1980)).

In addition to prokaryotes, eukaryotic microbes, such as yeast may also be used. *Saccharomyces cerevisiae,* or common baker's yeast is the most commonly used among eukaryotic microorganisms, although a number of other strains are commonly available. For expression in *Saccharomyces,* the plasmid YRp7, for example, (Stinchcomb et al., *Nature* 282, 39 (1979); Kingsman et al., *Gene* 7, 141 (1979); Tschemper et al., *Gene* 10, 157 (1980)) is commonly used. This plasmid already contains the trp1 gene which provides a selection marker for a mutant strain of yeast lacking the ability to grow in tryptophan, for example ATCC No. 44076 or PEP4-1 (Jones, *Genetics* 85, 12 (1977)). The presence of the trp1 lesion as a characteristic of the yeast host cell genome then provides an effective environment for detecting transformation by growth in the absence of tryptophan.

Suitable promoting sequences in yeast vectors include the promoters for 3-phosphoglycerate kinase (Hitzeman et al., *J. Biol. Chem.* 255, 2073 (1980)) or other glycolytic enzymes (Hess et al., *J. Adv. Enzyme Reg.* 7: 149 (1968); Holland et al., *Biochemistry* 17 4900 (1978). Other promoters, which have the additional advantage of transcription controlled by growth conditions, are the promoter region for alcohol dehydrogenase 2, isocytochrome C, acid phosphatase, degradative enzymes associated with nitrogen metabolism, and the aforementioned glyceraldehyde-3-phosphate dehydrogenase, and enzymes responsible for maltose and galactose utilization. Any plasmid vector containing yeast-compatible promoter, origin of replication and termination sequences is suitable.

In addition to microorganisms, cultures of cells derived from multicellular organisms such as mammals and insects may also be used as hosts. In principle, any such cell culture is workable, whether from vertebrate or invertebrate culture. However, interest has been greatest in vertebrate cells, and propagation of vertebrate cells in culture (tissue culture) has become a routine procedure in recent years (*Tissue Culture*, Academic Press, Kruse and Patterson, editors (1973)). Examples of such useful host cell lines are VERO and HeLa cells and Chinese hamster ovary (CHO) cells. Expression vectors for such cells ordinarily include (if necessary) an origin of replication, a promoter located upstream from the gone to be expressed, along with any necessary ribosome binding sites, RNA splice sites, polyadenylation sites, and transcriptional terminator sequences.

For use in mammalian cells, the control functions on the expression vectors are often provided by viral material. For example, commonly used promoters are derived from polyoma, Adenovirus 2, and most frequently Simian Virus 40(SV40). The early and late promoters of SV40 virus are particularly useful because both are obtained easily from the virus as a fragment which also contains the SV40 viral origin of replication (Fiers et al., *Nature* 273, 113, (1978)). Smaller or larger SV40 fragments may also be used, provided there is included the approximately 250 bp sequence extending from the HindIII site toward the BgII site located in the viral origin of replication. Further, it is also possible, and often desirable, to utilize promoter or control sequences normally associated with the desired gene sequence, provided such control sequences are compatible with the host cell systems.

An origin of replication may be provided either by construction of the vector to include an exogenous origin, such as may be derived from SV40 or other viral (e.g Polyoma, Adeno, VSV, BPV) source, or may be provided by the host cell chromosomal replication mechanism. If the vector is integrated into the host cell chromosome, the latter is often sufficient.

Upon transformation of the selected host with an appropriate vector, the antigenic polypeptide or fragment encoded can be produced often in the form of a fusion protein by culturing the host cells. The fusion protein including the polypeptide or fragment is then recovered and purified as necessary. Recovery and purification can be achieved using any of those procedures known in the art, for example by adsorption onto and elution from an anion exchange resin. As will be apparent from the specific examples provided, the carrier portion of the fusion protein can prove useful in this regard.

The purification procedure adopted will of course depend upon the degree of purity required for the use to which the polypeptide or fragment is to be put. For most vaccination purposes, separation of the fusion protein from the remaining components of the cell culture is sufficient. However, in cases where a greater degree of purity is desired, the carrier component of the fusion protein can be cleaved from the antigenic component. As will again be apparent from the specific examples provided, this can be easily achieved through the provision of an appropriate enzyme cleavage site between the carrier component and the antigen.

Where is as preferred, recombinant techniques are used to produce the antigenic polypeptide, the first step is to obtain DNA encoding the desired product. Such DNA molecules comprise still a further aspect of this invention.

The DNA molecule of the invention preferably encodes an active fragment of the native polypeptide. More particularly, the DNA molecule comprises the nucleotide sequence extending from nucleotides 1 to 522 of the sequence of FIG. 2, the nucleotide sequence extending from nucleotides 1 to 658 of the sequence of FIG. 2, or the entire nucleotide sequence of FIG. 2.

This molecule can be isolated from an appropriate natural source or can be produced as intron-free cDNA using conventional techniques such as those used in the specific description set out hereinafter.

However, as indicated above, the invention also contemplates variants of the polypeptide and its fragments which differ from the native amino acid sequences by the insertion, substitution or deletion of one or more amino acids. Where such a variant is desired, the nucleotide sequence of the native DNA molecule is altered appropriately. This alteration can be made through elective synthesis of the DNA or by modification of the native DNA by, for example, site specific or cassette mutagenesis.

Once obtained, the DNA molecule is treated to be suitable for insertion together with the selected control sequence into the appropriate cloning and/or expression vector. To this end the DNA is cleaved, tailored and religated as required.

Cleavage is performed by treating with restriction enzyme(s) in a suitable buffer. Any of the large number of commercially available restriction enzymes can be used as specified by the manufacturer. After cleavage, the nucleic acid is recovered by, for example, precipitation with ethanol.

Tailoring of the cleaved DNA is performed using conventional techniques. For example, if blunt ends are required, the DNA may be treated with DNA polymerase I (Klenow), phenol and chloroform extracted, and precipitated by ethanol.

Re-ligation can be performed by providing approximately equimolar amounts of the desired components, appropriately tailored for correct matching, and treatment with an appropriate ligase (eg $T_4$ DNA ligase).

In addition to the protective antigens of the invention and the method of producing these, a further and most important aspect of the present invention relates to the use of the protective antigen as the active agent in a ruminant vaccine against *T.ovis* infection. In this aspect, the protective antigen of the invention can be administered either alone or in the form of a vaccine comprising the protective antigen of the invention as the active ingredient together with a pharmaceutically acceptable diluent carrier or adjuvant.

Examples of suitable adjuvants known to those skilled in the art are saponins (or derivative or related material), muramyl dipeptide, trehalose dimycollate, Freunds's complete adjuvant, Freund's incomplete adjuvant, other water-in-oil emulsions, double emulsions, dextran, diethylaminoethyl-dextran, potassium alum, aluminium phosphate, aluminium hydroxide, bentonite, zymosan, polyelectrolytes, retinol, calcium phosphate, protamine, sarcosine, glycerol, sorbitol, propylene glycol, fixed oils and synthetic esters of higher fatty acids. Saponins have been found to be particularly effective adjuvants.

The protective antigen of the invention may also be treated in any conventional way to enhance its stability or to conserve or potentiate its immunogenic efficacy. For example, the antigen may be treated with a suitable inhibitor, modifier, crosslinker or denaturant in such a way as to enhance its immunogenicity.

In addition, the protective antigen can be administered in combination with other therapeutic agents such as anthelmintics, for example levamisole, or other vaccines.

The vaccine can be administered to the ruminant by any of those methods known in the art. However, the preferred mode of administration of the vaccine is parenteral. The term "parenteral" is used herein to mean intravenous, intramuscular, intradermal and subcutaneous injection. Most conveniently, the administration is by subcutaneous injection.

The amount of the vaccine administered to the ruminant to be treated will depend on the type, size and body weight of the ruminant as well as on the immunogenicity of the vaccine preparation. Conveniently, the vaccine is formulated such that relatively small dosages of vaccine (1 to 5ml) are sufficient to protect-the ruminant.

The immunogenicity of the antigenic polypeptide of the invention and its effectiveness as the active agent of a ruminant vaccine will be appreciated from the immunogenicity trials detailed in the Examples 4 and 5.

As yet a further aspect of the invention the use of the DNA molecule described above or a subsequence thereof as a probe is contemplated. In this aspect, the DNA molecule is used to indentify by hybridisation DNA of a cestode parasite such as *T. saginata*, *T. hydatigena* or *E. granulosus* which encodes an immunogenic antigen of that parasite. In this way, further parasite antigens suitable for use in a vaccine can be identified.

An immunogenicity trial has been conducted to test whether protection against infection by *T. hydatigena* can be generated by the protective *T.ovis* antigen of the present invention. The details and results of this trial is set out in Example 8 below.

Reference to Example 8 shows that a reduction in *T. hydatigena* cysts is achieved between non-vaccinated animals and animals vaccinated with the GST-45W fusion protein of the present invention. This establishes the existence of significant areas of homology between the amino acid sequences encoding the protective antigens of *T. ovis* and *T. hydatigena* which in turn validates the use of the DNA molecule of the invention or a subunit thereof as a probe to identify the DNA encoding the protective antigen of *T. hydatigena*.

The method of use of the DNA molecule of the invention as a probe will be well understood by those persons skilled in the art. For example, those techniques set out in Maniatis, et al; "Molecular Cloning: A Laboratory Manual", Cold Spring Harbour (1982) could be used.

The results of Example 8 also show that the protective antigen of the invention can be employed in the vaccination of ruminants against cestode parasites other than *T.ovis*.

Similarly to the use of the DNA molecules of the invention to identify DNA encoding the corresponding protective antigen of other cestode parasites, antibody probes specific for the protective antigens of the invention can be used to screen the antigens expressed by organisms transformed by the DNA of the cestode in question. The location of a positive clone (one expressing an antigen recognised by the antibody) will allow identification of both the protective antigen itself and the DNA which encodes it. Such antibody probes can be either polyclonal or monoclonal and can be prepared by any of those techniques known in the art. For example, a suitable procedure by which polyclonal antibody probes can be prepared is set out in Example 2.

Monoclonal antibodies can be prepared in accordance with the procedure of Kohler and Milstein (Kohler G and Milstein C, "Continuous cultures of fused cells secreting antibody of predefined specificity," *Nature* 256, 495–497 (1975)).

Specific non limiting examples of the invention will now be described.

EXAMPLE 1

This experiment showed that it was possible to immunise sheep with polyacrylamide gel fractions containing antigens solubilised in SDS.

*T.ovis* eggs were solubilised in 2% SDS PAGE sample buffer, heated to 95° C. for 3 minutes and centrifuged at 100,000 g for 1 hour. Approximately 9 million egg equivalents were loaded onto two 3 mm thick gradient gels consisting of 5–30% polyacrylamide using the method of Laemmli (*Nature,* 277, 680 (1970)).

After electrophoresis overnight, two side lanes and one central lane were excised from the slab gels and the proteins were electrophoretically transferred to nitrocellulose paper using a Bio-Rad Trans-Blot cell. Once transferred, the proteins were reacted with rabbit antiserum to oncosphere antigens according to the method of Towbin et al; supra (1986). Following development of the immunoblots, the nitrocelluslose strips were laid alongside the remaining gel slices so that fractions could be cut from appropriate regions of the gel.

Fractions were homogenised with an incomplete oil adjuvant and injected subcutaneously on two occasions into groups of five sheep. One complete vertical strip of gel was saved from each run and was also homogenised with adjuvant and injected. Control sheep were injected with homogenised polyacrylamide and adjuvant only.

All sheep were challenged infected with 1500 eggs two weeks after the second injection and carcases were examined for cysts two weeks later.

Post mortem results are shown in Table 1:

| Group | Substance Injected | Cyst Numbers At Post Mortem | Mean | % Protection |
|---|---|---|---|---|
| ADJUVANT CONTROL | Acrylamide + Adjuvant | 0, 8, 12, 13, 13 | 9 | — |
| UNFRACTIONATED ANTIGEN | Unfractionated SDS antigen + acrylamide + adjuvant | 0, 0, 0, 0, 0 | 0 | 100 |
| 47-52 KDA FRACTION | 47-52 K Da polypeptides in SDS + acrylamide + adjuvant | 0, 0, 0, 0, 1 | 0, .2 | 98 |

The results show that a native polypeptide antigen having a molecular weight of 47–52 kD as calculated by SDS- PAGE is effective in generating a protective response to *T. ovis* infection.

EXAMPLE 2

(a) Production of Antibody Probes

A preliminary step in the technique used in the present invention involved the production of antibody probes specific to the 47–52 kD antigen fraction identified by the inventors. As will be appreciated, such probes are commonly used for screening the products of expression of a population of host organisms or cells transformed by an expression vector in order to allow the organisms or cells expressing the required product to be identified.

The specific antibody probes of the invention were formed as follows.

*T.ovis* oncosphere antigens were solubilized by brief ultrasonic disruption and centrifuged at 100,000g for one hour. The antigens thus solubilised were separated by SDS PAGE according to the method of Laemmli (*Nature*, London 277, 680 (1970)). Proteins were routinely separated by SDS PAGE in gradient gels composed of linear polyacrylamide concentrations between 12 to 18%. Electrophoresis was performed using an LKB vertical electrophoresis system.

Following SDS PAGE the proteins were electrophoretically transferred to nitrocellulose paper using a Bio-Rad Trans-Blot cell. Transfer conditions were 90 volts constant voltage for four hours at 10° C.

After transfer, unreacted sites were blocked by incubating the nitrocellulose in 20mM tris HCl pH 7.4 containing 2% casein hydrolysate, 0.5M NaCl and 0.5% tween 20 for four hours at ambient temperature on a rocking platform.

Antibodies specific to the 47–52 kD antigen fraction were obtained using the Beall and Mitchell technique (*J. Immunological Methods* 86 217–223 (1986)), for eluting specific antibodies from nitrocellulose blots. The antigen was located on the nitrocellulose blot using an anti-oncosphere antiserum obtained from rabbits hyperimmunised with *T. ovis* oncosphere antigens. The antibodies specific to the 47–52 kD antigen fraction were eluted with 0.1M glycine HCl pH 2.8, neutralised and concentrated for later use.

(b) Recombinant expression of 47–52 kD antigen fraction (i) Formation of a cDNA Library and initial identification of antigen-coding material

*Taenia ovis* eggs were stored at 4° C. for no more than one week. After hatching and activation, oncospheres were cultured in vitro for 2–3 hours in EMEM, washed twice in sterile saline, frozen in liquid nitrogen and stored at −230° C.

For RNA extraction, frozen oncospheres were ground to a paste in liquid nitrogen and RNA isolated using the guanidine-HCl procedure (Kemp D. J. et al. *Proc. Natl. Acad Sci USA* 80 3787–3791 (1983)). 20 to 50 ug of pooled total, RNA was fractionated over oligo-dT cellulose (Aviv H and Leder P. *Proc Natl. Acad Sci USA* 69 1408–1412 (1972)) and poly A+RNA was recovered. This was then converted into cDNA using the cDNA synthesis kit from Amersham as described in the product manual with two exceptions:
(i) Having allowed the first strand reaction to proceed for 1 hour, a second aliquot of reverse transcriptase and Human Placental Ribonuclease inhibitor were added and the reaction continued for a further 40 minutes.
(ii) The repair step with T4 DNA polymerase was extended from 10 minutes to 30 minutes.

Double-stranded cDNA was methylated with Eco R1 methylase (Biolabs) and ligated to an equal mass of phosphorylated EcoR1 linker (Biolabs) for 72 hours at 12° C.

Linkered cDNA was digested with Eco R1 at 37° C. overnight and cDNA molecules separated from free linkers by passage over sepharose 4B (Pharmacia). cDNA molecules of size greater than 400 base pairs were recovered and pooled.

cDNA was subsequently ligated to EcoR1—restricted, de-phosphorylated lambda gt11 DNA (Promega Biotech) and aliquots of the ligation were packaged in vitro (Promega Biotech) and plated on *E. coli* strain ST9 (Bowtell DDL et al. *Parasitology* 93, 599–610 (1986)). The oncosphere library consisted of $7.5 \times 10^5$ individual recombinants.

For screening, aliquots of the library were plated on ST9 and screened for antigen—positive clones as described by Young and Davis (*Proc. Natl. Acad. Sci. USA* 80, 1194–1198 (1983)).

Nitrocellulose filters were probed with the affinity purified anti 47–52 kD antibodies prepared as described above. Positive clones producing antigenic components according to one aspect of the invention were picked and rescreened at low density to confirm identity.

A number of cDNA clones identified as above as expressing antigenic components reactive with anti—*T. ovis* 47–52 kD affinity—purified antibody ('45'_clone type) were arrayed in a microtitre tray. The clones were divided into two groups on the basis of immunoreactivity with rabbit anti *T. ovis* oncosphere serum—those that reacted weakly ('W') and those reacting strongly ('S'). Two cDNA clones expressing *T. ovis* antigens were accordingly termed 45W and 45S.

(ii) Deposition of Clones In The American Type Culture Collection

Phage DNA was purified from each of the clones 45W and 45S and the cDNA inserts for each clone subsequently isolated from the phage DNA.

The cDNA inserts were ligated to EcoRI-cut pUR 292 DNA (Ruther and Muller-Hill, *Embo. J.* 2 1791–1794 (1983)) and transformed into *E.coli* strain JM101 (Bankier and Barrell, from 'Techniques in Nucleic Acid Biochemistry', B508 shotgun DNA sequencing, Flavell Ed. Elsevier). Recombinants expressing *T.ovis* antigens were detected using the procedure described by Young & Davis (*Proc. Natl. Acad Sci USA* 80 1194–1198 (1983)).

Nitrocellulose filters were probed with affinity-purified antibody probes specific to 47–52 kD antigen fraction prepared as described above. Two antigen- positive clones were picked and rescreened at low density to confirm identity.

The cloned organisms expressing the respective *T.ovis* antigens have been designated *E.coli* 45W and *E.coli* 45S respectively. Each clone is a gram negative rod which is ampicillin resistant. A sample of both *E.coli* 45W and *E.coli* 45S has been deposited at the American Type Culture Collection, Rockville, Md. 20852, USA under ATCC designation numbers 67507 and 67506 respectively.

(iii) Production and Purification of the Antigen Fraction

Although any of those suitable expression vectors known in the art could have been used to express the protective antigen of the invention, the applicants elected to use an expression vector which is based on the enzyme glutathione S-transferase (GST) (E.C 2.5.18) due to the advantages of such vectors. In particular, the applicants elected to use as the expression vector a plasmid which expresses the antigen of the invention as a fusion protein with a Mr 26,000 glutathione S-transferase encoded by the parasitic helminth *Schistosoma japonicum*. (Smith et al., (*Proc. Natl. Acad. Sci. USA* 83 8703–8707 (1986)).

The vector used can be constructed as follows. Multiple cloning sites were created in the pSj1 Sj26 cDNA (Smith et al., (1986) supra; Smith et al., *Proc. Natl. Acad. Sci, USA* 84, 6541 (1987)) through the introduction of a BamHI linker at the unique MnlI cleavage site so that the TAA translation termination codon of Sj26 was replaced with the sequence TCGGATCC. The 5'-terminus of the pSj1 cDNA was also altered through the replacement of the 5'-terminal EcoRI-Sau96i fragment with oligonucleotides containing a BamHI cleavage site followed by the sequence CACCATGTCC and then nucleotides 12–38 of the pSj1 cDNA, so producing a BamHI fragment encoding native Sj26. This BamHI fragment was inserted into the BamHI site of pIC19H (Marsh et al., *Gene* 32, 481–485 (1984)) such that the cDNA 3'-terminus was followed by unique SmaI, EcoRI, ClaI and EcoRV cleavage sites. A blunt-ended BamHI-EcoRV fragment containing the reconstructed Sj26 cDNA was inserted into the PvuII site of ptac12 Eco (ptac12 (Amann et al., *Gene* 25, 167–178) (1983)) modified by filling in the unique EcoRI site and religation) in the correct orientation for transcription from the tac promoter. This plasmid (pSj10) was further modified through the introduction of an oligonucleotide (5'-TGACTGACTGA-3') encoding stop codons in all three frames into the blunt-ended ClaI site at the cDNA 3'-terminus, while the BamHI cleavage site at the cDNA 5'-terminus was deleted by filling in using PolIk.

The resulting vector is known as plasmid pSj10 Bam7stop7 and is the vector used in the present invention. This vector is described by Smith D. B and Johnson K. S (*Gene* 67, 31–40 (1988)) in the caption to FIG. 1. The antigen-coding cDNA of clones 45W and 45S was then inserted into the vector and the resulting plasmids (pSj 45W, pSj 45S) transformed into *E.coli* strain JM109 (Yanisch-Perron et al *Gene* 33 103–119 (1985)). Overnight cultures of the transformed hosts containing the pSj 45W and pSj 45S were diluted 1:10 in 800 ml of fresh medium and grown for 1 hour at 37° C. before adding IPTG to 0.1 mM. After a further 3–7 hours of growth cells were pelleted and resuspended in 1/50–1/100 culture volume of mouse tonicity phosphate-buffered saline (MTPBS) (150 mM NaCl, 16mM $Na_2HPO_4$, 4 mM $NaH_2PO_4$ (pH 7.3)).

The *T.ovis* antigen produced by each host cell culture is expressed as a COOH- terminal fusion protein with an approximately Mr 27,500 protein which includes a Mr 26000 *S. japonicum* enzyme glutathione S-transferase (GST) as the carrier protein.

The molecule weight of the *T.ovis* polypeptide fragment expressed was calculated to be approximately 26 kD by SDS-PAGE (date not shown).

To extract this fusion protein from the host cell cultures, the following procedure was adopted. Cells were lysed on ice by mild sonication and after adding Triton X-100 (BDH Chemicals) to 1%, were subjected to centrifugation at 10,000 g for 5 minutes at 4° C. The supernatant was mixed at room temperature in a 50 ml polypropylene tube on a rotating platform with 1–2 ml 50% glutathione-agarose beads (sulphur linkage, Sigma) for 30 minutes. Before use, beads were pre-swollen in MTPBS, washed twice in the same buffer and stored in MTPBS at 4° C. as a 50% solution (v/v). After absorption, the beads were collected by centrifugation at 500g for 10 seconds and washed three times with 5ml MTPBS. Fusion protein was eluted by competition with free glutathione using 2×1 bead volume of 50 mM Tris-HCl (pH 8.0) containing 5 mM reduced glutathione (Sigma) (final pH 7.5. freshly prepared) for five minutes.

EXAMPLE 3

A second experiment was conducted to express the 26 kD antigenic polypeptide fragment of the invention in the pGEX vector system. This vector system is described by Smith, D B and Johnson, K S (*Gene*, (1988) supra) and is the subject of Australian Patent Application PI 2195/87 entitled "Novel Fusion Protein", the disclosure of which is incorporated by reference.

Plasmid DNA of pSj10 Bam7Stop7-45W was digested with the restriction endonuclease Eco-RI and the cDNA insert of 45W was then purified by DEAE elution from an agarose gel. The insert was then ligated with Eco-RI digested pGEX-1 and transformed into *E.coli* strain JM 101 (Bankier and Barrell, supra).

Overnight cultures of the transformed hosts containing the pGEX-1-45W were grown in four 1.4 litre fermenters for 6 hours in SOB medium enriched for peptone (2.75%) and yeast extract (0.65%) and containing 0.1 mg/ml ampicillin. After 3 hours growth, fusion protein expression was induced by addition of IPTG to 0.021 mg/ml and culturing continued for a further 3 hours. Bacteria were pelleted by centrifuging at 5000 g for 20 mins and stored overnight at −18° C.

Cell pellets were resuspended to 20% w/v in 0.1M PBS pH7.2 containing 0.5% Triton X-100 and were sonicated on ice in 10 ml volumes at 15 watts for 1 minute.

Lysates were centrifuged at 5000 g for 20 minutes and the supernatants held at 4° C. until processed.

20 ml glutathione-agarose (GSH-agarose, Sigma, sulphur linkage) was placed in a 150 ml sintered glass filter and washed with 5×100 ml PBS. After closing the outlet, *E. coli* lysate was added and mixed occasionally over 20 minutes. The lysate was run off, collected and stored for future analysis. GSH-agarose was washed 5×100 ml PBS and bound material was eluted by reacting the gel with 20 ml of 5mM glutathione, reduced form, in 50 mM tris HCl pH7.8. After 5 minutes the eluate was collected and the gel rinsed with a further 10 ml glutathione.

It will of course be appreciated that should further purification of the antigenic component of the invention be required, plasmids modified to permit cleavage of the GST portion from the remainder of the fusion protein can be used. For example, vectors pGEX-2T or pGEX-3X as described in Smith, D B and Johnson, K S (*Gene* (1988) supra) could be used.

EXAMPLE 4

(a) Determination of Immunity Induced by the Cloned Antigens

Initial vaccination trials were conducted to establish the effectiveness of the cloned antigens, GST 45W and GST 45S produced by Example 2 in inducing protective immunity in sheep. In the initial trials, the immunogenic ability of each antigen as a fusion protein was compared.

The immunogenicity trial was conducted as follows.

The fusion proteins, oncosphere antigen, and GST vector control were emulsified with an incomplete oil adjuvant (Bokhout B. A. et al *Vet. Immunol. Immunopath.* 2 491–500 (1981)) and injected subcutaneously into sheep on three separate occasions using dose rates given in Table 2 below.

Three weeks after the third injection all sheep were infected with approximately 5000 viable *T.ovis* eggs. Six weeks later, sheep were humanely slaughtered and the masseter muscles, heart and diaphragm were examined for the presence of cysts.

Cyst numbers are shown in Table 2.

There was a significant reduction in cyst numbers in the groups of sheep injected with either cloned antigen GST 45W or the mixture of the two cloned antigens (66=reduction; $p \leq 0.01$). However no protective immunity was seen with the cloned antigen GST 45S and hence the immunity seen in the pooled group resulted from the GST 45W cloned antigen. This result demonstrates that cloned antigen GST 45W induces a signficant level of immunity in sheep against infection with T.ovis.

TABLE 2

| Antigen | | 1° Injection | 2° Injection | 3° Injection | Total antigen dose (Per Sheep) |
|---|---|---|---|---|---|
| | | \multicolumn{3}{c}{Immunising Dose (per Sheep)} | |
| Oncosphere Equivalents | | $10^5$ | $10^5$ | $10^5$ | $3 \times 10^5$ |
| PBS | | — | — | — | — |
| GST 45S + GST 45W | } Pooled | 6.7*+ 7.5 | 6.7+ 7.5 | 35+ 35 | 48+ 50 |
| GST 45S + GST 45W | } Pooled and SDS Treated | 6.7*+ 7.5 | 6.7+ 7.5 | 35+ 35 | 48+ 50 |
| GST 45S | | 6.7 | 6.7 | 35 | 48 |
| GST 45W | | 7.5 | 7.5 | 35 | 50 |
| GST Vector | | 7.8 | 7.8 | 200 approx | 215 approx |

*Values are ug protein based on $OD^{280}$ estimates relative to GST-Vector.

| Immunisation Schedule | | | | |
|---|---|---|---|---|
| Week 0 | Week 3 | Week 6 | Week 9 | Week 15 |
| 1° Injection | 2° Injection | 3° Injection | Challenge | Post Mortem |

TABLE 3

Numbers of T. ovis cysticerci in sheep vaccinated with fusion proteins GST 45W and GST 45S

| Group | *Cyst Numbers in each sheep | Mean |
|---|---|---|
| Antigen control | 0, 1, 1, 1 | 0.75 |
| Adjuvant control | 68, 95, 105, 109 | 94 |
| GST Pool | 0, 15, 18, 59 | 23+ |
| GST Pool SDS Treated | 31, 36, 56, 141 | 66 |
| GST 45S | 40, 74, 104, 161 | 95 |
| GST 45W | 11, 12, 24, 68 | 29+ |
| GST Vector | 46, 69, 106, 116 | 84 |

+ p < 0.01 compared to adjuvant control plus GST vector (t test); p < 0.05 compared to GST vector alone (t test).
*Cyst numbers are for masseters, heart and diaphragm.

Figure 1:
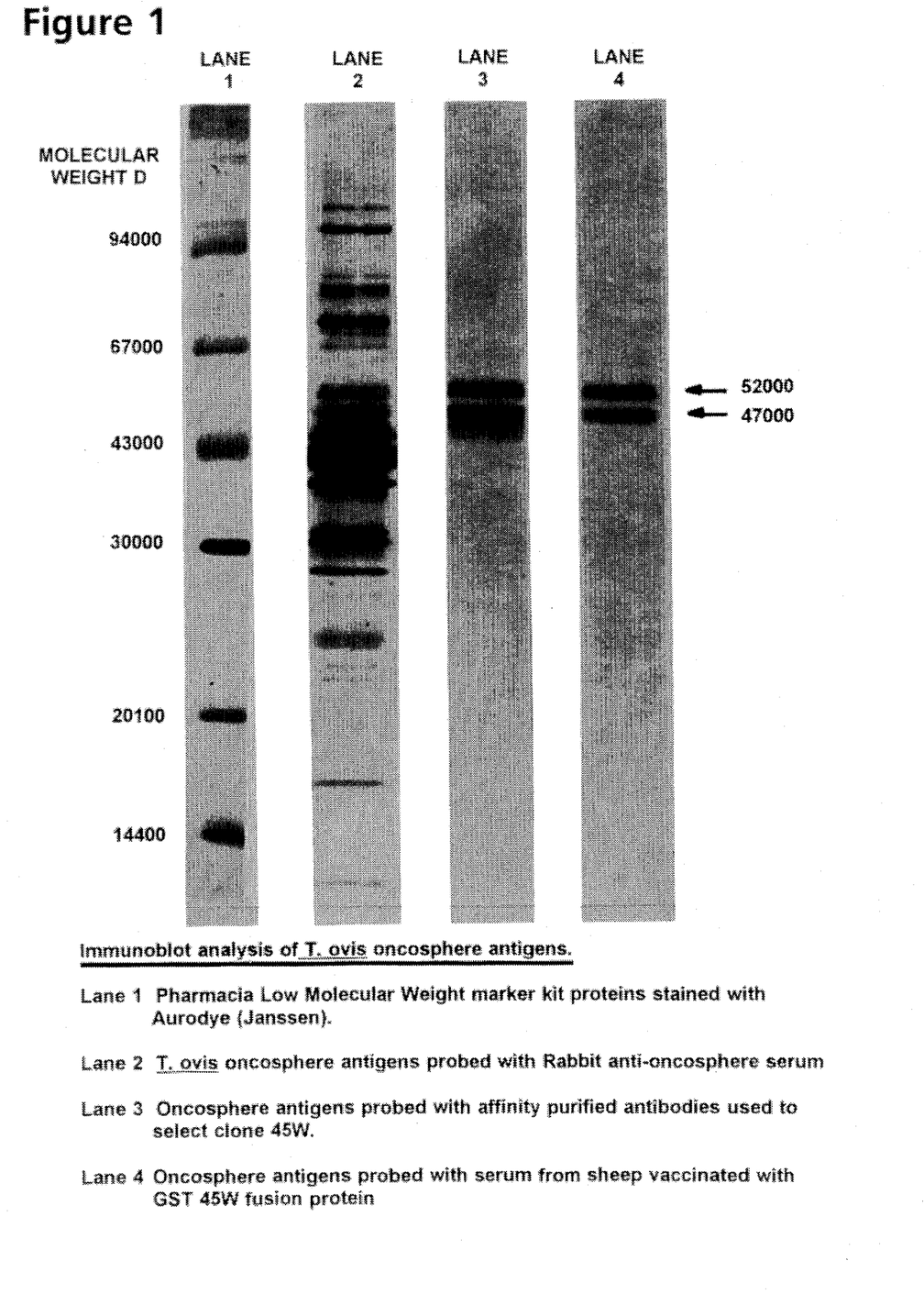
FIG. 1 is an immunoblot analysis showing that antibodies generated against the cloned GST 45W antigen recognise the native *T.ovis* antigen(s) having a molecular weight of 47–52 kD.

As a cross-check on the identity of the cloned GST 45W antigen, serum samples were taken from the sheep after 3 injections of the antigen and were analysed for the presence of antibody by reacting diluted sera with oncosphere antigens transferred to nitrocellulose using a Bio-Rad Trans Blot cell as before. FIG. 1 shows that sheep injected with the cloned GST 45W antigen of the invention had made antibodies which recognised the native T.ovis polypeptide with a molecular weight of 47–52 kD.

(b) Confirmation of Immunity Induced by Cloned Antigen 45W

A second trial was conducted to confirm the immunogenicity of the cloned 45W antigen and to see if a greater level of protection could be generated using different adjuvants.

The experimental protocol is set out in Table 4.

TABLE 4

Antigens, adjuvants and antigen doses used in the second vaccination trial with fusion protein GST 45W.

| Antigen | Adjuvant | 1° | 2° | 3° | Total (Per Sheep) | No of Sheep |
|---|---|---|---|---|---|---|
| | | \multicolumn{3}{c}{Immunising Dose (per sheep)} | | |
| Oncosphere Equivalents | Oil[1] | $0.5 \times 10^5$ | $0.5 \times 10^5$ | $0.5 \times 10^5$ | $1.5 \times 10^5$ | 5 |
| GST | Oil | 7.5[2] | 7.5 | 35 | 50 | 10 |
| GST 45W | Oil | 7.5 | 7.5 | 35 | 50 | 10 |
| GST 45W | Oil | 35 | 7.5 | 7.5 | 50 | 5 |
| GST 45W | Oil | 100 | 100 | 100 | 300 | 5 |
| GST 45W | Saponin | 7.5 | 7.5 | 35 | 50 | 5 |
| GST 45W | FCA[3] | 7.5 | 7.5 | 35 | 50 | 5 |
| GST | FCA | 7.5 | 7.5 | 35 | 50 | 5 |

[1] = Oil adjuvant (Bokhout B. et al Vet. Immunol. Immunopathol. 2 491–500 (1981)).
[2] = Values are ug protein based on $OD^{280}$ estimates relative to GST vector.
[3] = Freund's complete adjuvant (Difco).

Two weeks after the third injection of antigen all sheep were infected with approximately 2000 viable T. ovis eggs. Six weeks later, sheep were humanely slaughtered and the heart, diaphragm and entire body musclature were examined for the presence of cysts by finely slicing all muscle tissue. Cyst numbers are shown in Table 5.

TABLE 5

Numbers of T. ovis cysticerci in sheep vaccinated with fusion protein GST 45W.

| Group | *Cyst Numbers in each sheep | Mean |
|---|---|---|
| Oncosphere | 0, 0, 0, 0 | 0 |
| GST 50 ug Oil | 11, 16, 17, 18, 20 25, 29, 45, 48, 57 | 28.6 |
| GST 45W 50 ug Oil | 0, 0, 0, 0, 2 4, 6, 16, 18, 25 | 7.1+ |
| GST 45W 50 ug Oil | 0, 1, 3, 6, 26 | 7.2++ |
| GST 45W 300 ug Oil | 0, 0, 1, 7, 9 | 3.4++ |
| GST 45W 50 ug Saponin | 0, 0, 0, 1, 7 | 1.6+ |
| GST 4SW 50 ug FCA | 0, 0, 0, 2, 29 | 6.2++ |
| GST 50 ug FCA | 14, 15, 28, 44, 46 | 29.4 |

+ P < 0.01 compared to GST control group.
++ P < 0.05 compared to GST control group.
*Cyst numbers are for total carcase musclature.

Immunisation with cloned antigen GST 45W resulted in a highly significant reduction in cyst numbers compared to sheep given control protein GST.

The antigen was effective in stimulating immunity when injected with an incomplete oil adjuvant, saponin or FCA.

The results of the second immunogenicity trial confirm the ability of the fusion protein GST 45W encoded by pSj 45W to stimulate a protective immune response.

EXAMPLE 5

The following immunogenicity trial had employed the antigenic polypeptides produced in accordance with Example 3.

Groups of ten sheep were immunised by subcutaneous injections of 7.5, 7.5 and 35 ug of control protein GST or GST 45W (from pGEX-1-45W) on three occasions with three weeks between each injection. Saponin (1 mg) was included with each injection. Two weeks after the third injection all sheep were challenge infected with 2000 *T.ovis* eggs and two weeks later, the carcases were examined for the presence of cysts.

Number of cysts in each sheep found at post mortem examination are shown in the table.

| Group | Number of Cysticerci | Total | Mean |
|---|---|---|---|
| GST CONTROL | 2, 7, 8, 10, 12 19, 25, 28, 33 | 144 | 16.0 |
| GST 45W (pGEX-1-45W) | 0, 0, 0, 0, 2, 2, 3, 3, 4, 4, 5 | 20 | 2.0 |

This result showed that vaccination with GST 45W made with plasmid pGEX-1-45W reduced infection by 86% compared to controls (significant at $p<0.05$).

EXAMPLE 6

Nucleotide Sequencing of DNA Clone 45W

The cDNA of clone 45W has been sequenced to determine the nucleotide sequence and the amino acid sequence of the antigen it encodes.

The approach taken to generate the complete nucleotide sequence of clone 45W *T. ovis* cDNA was to (1) produce a series of deletion clones, using exonuclease III (Henikoff, S., *Gene* 28, 351–359 (1984)), that contained overlapping regions of 45W cDNA and (2) sequence the clones by the dideoxy chain termination method (Sanger et al., *Proc Natl. Acad. Sci. USA* 74, 5463–5467 (1977)).

This method involved the cloning of an approximately 1.0 kb EcoR1 fragment of 45W *T. ovis* cDNA into the EcoR1 site of the cloning vector M13mp18 (Norrander et al., *Gene* 26, 101–106 (1983)) in both orientations. Two clones with 45W cDNA inserted in either orientation were chosen by sequencing the ends of the 45W cDNA. This allowed the sequencing of both strands of 45W cDNA so that the sequence data of one strand could be verified with the other.

A number of deletion derivatives of these two clones were then generated after digestion with Exo III. This was necessary as it is not possible to read the complete nucleotide sequence of the 1.0 Kb Eco RI fragment from a single clone.

The clones were sequenced and the complete sequence of 45W cDNA was shown to be 928 bp in size. Details of the nucleotide sequence and the amino acid composition of its encoded polypeptide are shown in FIG. 2.

EXAMPLE 7

This experiment was performed to extablish the immunogenicity of polypeptide fragments encoded by subsequences of the DNA of FIG. 2.

The entire 45W complementary DNA (cDNA) was cloned into the Eco RI site of the vector pUC18 (Yanisch-Perron *Gene* 33, 103–119 (1985)) prior to cloning into the plasmid pGEX-2T (Smith and Johnson *Gene* (1988) supra). This plasmid pUC18-45W was digested separately with the restriction endonucleases Bam HI and Xho II or Barn HI and Hinc II. The DNA was electrophoresed on agarose Eels and the Bam HI/Xho II (658 bp) or Bam HI/Hinc II (542 bp) fragments containing 45W DNA were purified. These fragments were then ligated with pGEX-2T DNA digested with Bam HI in the case of the Bam HI/Xho HI fragment and transformed into the *E. coli* strain JM101 (Yanisch-Perron et al., 1985 supra). The Bam HI/Hinc II fragment was ligated with Bam HI/Sma I digested pGEX-2T DNA and this was also transformed into the same *E. coli* strain.

The appropriate clones were selected on the basis of their DNA insert size and molecular weight of their affinity purified GST fusion proteins (Smith and Johnson *Gene* (1988) supra). The approximate molecular weights of the *T.ovis* portions of the pGEX-2T-45W (Bam HI/Xho II) and (Bam HI/Hinc II) fusion proteins are 20000 and 16000 respectively. These fusion proteins when electrophoresed on a 13% SDS gel and stained with Coomassie blue appeared to be stable.

The extent of the DNA sequences of the subclones pGEX-2T-45W (Bam HI/Xho II) and pGEX-2T-45W (Bam HI/Hinc II) are nucleotides 1-658 and 1-522 of FIG. 2, respectively.

Western blot analysis was performed with the fusion proteins prepared from pGEX-2T-45W (Bam HI/Xho II) and (Bam HI/Hinc II) and also pSj10 Bam7Stop7-45S and pGEX-2T-45W. These fusion proteins were electrophoresed on SDS-polyacrylamide gels, transferred to nitrocellulose and probed with the 45W specific monoclonal antibody 3F10F6 prior to incubation with $^{125}$I-labeled protein A.

Antibody 3F10F6 was prepared as follows;

BALB/c mice were immunised with GaT 45W fusion protein and hybridomas were prepared according to the method of Fazekas de St. Groth and Scheidegger (J. Immunological Methods 35 1–21, Production of Monoclonal Antibodies; Strategy and tactics (1980)). Monoclonal antibody 3F10F6 was selected by ELISA analysis of hybridoma supernatants against GST 45W, and was purified by the method of Reik et al (1987, J. Immunological Methods 100, 123–130).

Figure 3:
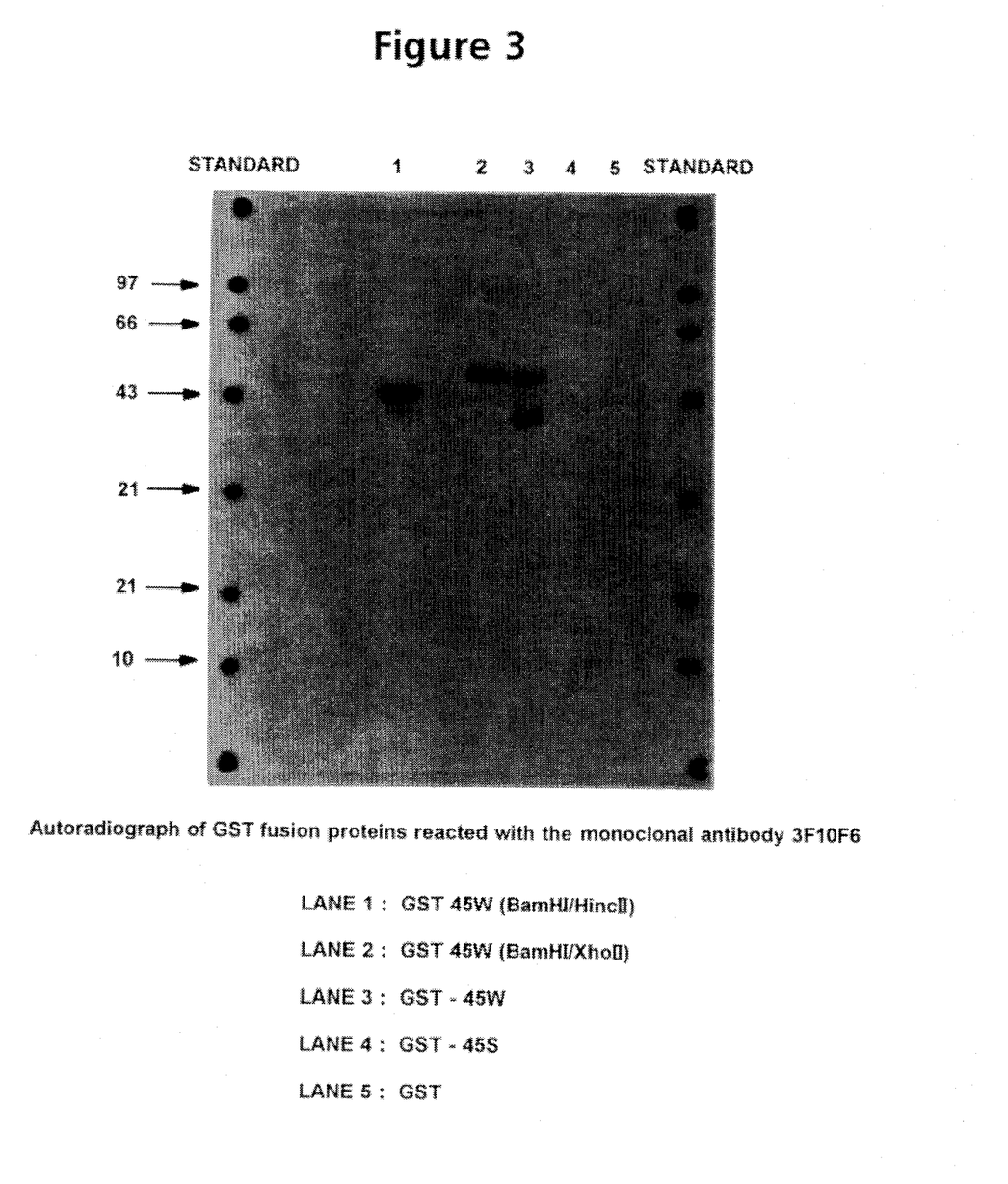
FIG. 3 is an autoradiograph showing that antibodies generated against the native 47–52 kD polypeptide antigen recognise the cloned subfragments of the GST-45W antigen.

The results are shown in FIG. 3. As can be seen by reference to this Figure, a positive reaction was obtained with antibody 3F10F6 in relation to the antigens expressed by host cells transformed with pGEX-2-45W (Bam HI/Xho II) and pGEX-2-45W (Bam HI/Hinc II). This indicates that the polypeptide fragments encoded by nucleotides 1 to 522 and 1 to 658 of FIG. 2 (which code for amino acids 1 to 172 and 1 to 217, respectively) are antigenic.

EXAMPLE 8

This experiment was conducted to assess the level of cross-protection, if any, which can be generated by the *T.ovis* polypeptide of the invention to infection by other cestode parasites. Any cross-protection found would support the existence of areas of significant homology between both the amino acid and nucleotide sequences of the antigenic determinants for both species and validate the use of both the DNA molecules and antibodies of this invention as probes.

Sheep were immunised with 4×100 ug injections of fusion protein produced as in Example 3 given subcutaneously together with 1 mg saponin in 2 ml saline. The immunising doses were given at two week intervals and sheep were challenge infected with 2000 *T. hydatigena* eggs two weeks after the final immunising dose.

Sheep were examined for cysts eight weeks after infection.

| | Viable Cysts | Degenerate Cysts | Total |
|---|---|---|---|
| Controls | 1 | 12 | |
| | 2 | 0 | |

|            | Viable Cysts | Degenerate Cysts | Total |
|------------|--------------|------------------|-------|
|            | 6            | 23               |       |
|            | 87           | 45               |       |
|            | 260          | 170              |       |
|            | 356          | 250              | 606   |

|            | Viable Cysts | Degenerate Cysts | Total |
|------------|--------------|------------------|-------|
| Vaccinates | 0            | 9                |       |
|            | 0            | 1                |       |
|            | 1            | 8                |       |
|            | 1            | 3                |       |
|            | 3            | 23               |       |
|            | 34           | 12               |       |
|            | 39           | 56               | 95    |

Overall the results show 84% reduction in cyst numbers between the groups.

In accordance with the present invention there is provided a polypeptide antigen of T.ovis together with active fragments of such a polypeptide which are effective in generating a protective immunological response against T.ovis infection in ruminants. It has been established that vaccination with this polypeptide and/or its fragments stimulates almost complete immunity against challenge infection with T.ovis eggs. It is the highest level of protection achieved thus far achieved in a natural host-parasite system by injection of a single antigen. The invention also provides a recombinant method for expression of the antigen by which commercial quantities can be obtained.

It will be appreciated that the above description is provided by way of example only and that variations in both the materials and the techniques used which are known to those persons skilled in the art are contemplated.

In accordance with the present invention there is provided a polypeptide antigen of T.ovis together with active fragments of such a polypeptide which are effective in generating a protective immunological response against T.ovis infection in ruminants. It has been established that vaccination with this polypeptide and/or its fragments stimulates almost complete immunity against challenge infection with T.ovis eggs. It is the highest level of protection achieved thus far in a natural host-parasite system by injection of a single antigen. The invention also provides a recombinant method for expression of the antigen by which commercial quantities can be obtained.

It will be appreciated that the above description is provided by way of example only and that variations in both the materials and the techniques used which are known to those persons skilled in the art are contemplated.

We claim:

1. A purified and isolated DNA molecule comprising a nucleotide sequence which encodes the amino acid sequence of FIG. 2, or comprising a fragment of said nucleotide sequence which encodes a polypeptide capable reducing the severity of T.ovis infection in a ruminant.

2. The DNA molecule of claim 1 comprising the nucleotide sequence

| 1   | GAATTCCCGG | ACTACGAACA | ACCCATCGAG | AGAACAGTGG | TAGAATATCC | ATCACTACGT |
|-----|------------|------------|------------|------------|------------|------------|
| 61  | GACATCTTTG | CTTGGGAACC | TCCGACTTCT | AACTCCATTG | GCCTAACTTG | GCAAAGGCAT |
| 121 | GCATTTCCTG | GTGTGGAACG | TGAAGTGCTC | ACATTGAAGG | CAGTGCCGAC | TTCTGAACCC |
| 181 | AATAACACCA | AGACAGCATA | TGCAAAGCTC | GGCAGCGGAA | AAGTCACTCT | TGATGGACTG |
| 241 | AAGCCCAATG | CCACATATCT | TGTGACTGCG | ACGGCAAATA | TAAGTGGAGA | CACAATTCTG |
| 301 | GTATTGAGCA | ATACTTTTCA | TACACTGGCC | AATGGCACAA | ATATTATAAA | TAACATCTTC |
| 361 | CATTGGGGTC | CTGTGACTAA | TCAATCAATT | CAAGTAAGAT | GGGATCAGAT | AAAACCGGAG |
| 421 | GAAACAAGCG | CTCTGATAGT | CACACTGACG | GCAGAGATGG | CTTCTGACCC | CGGAGTGGAA |
| 481 | AGATCGGAGT | CTGCACTCTT | CGGTAAAGGA | AAGGTCACTG | TTGACGGACT | GGAGTCCGAC |
| 541 | ACACTATATA | TTGCGACTGT | GATGGTATTT | AGAAATGGAA | GGCAATACTT | CAATTCCACC |
| 601 | AGAGATATTC | GAACACTCAA | ATCTGGCCAT | AAGGAGGTAA | CAGTCGTAAC | AACTAGTGGA |
| 661 | TCTGGTATAG | CCTCCACAAT | ACTTGGACTC | CTCCTCACCT | GCGTGGCGCT | AGTCCTTGCT |
| 721 | TGAACACTTG | CGTCGGTCAA | TGCCCATTTC | CAAACCATCC | ATCTTCATCC | AATCTCACGT |
| 781 | CCCATGACTT | GCTTGTCTGC | ACCACCTCTT | TCTACCTTGC | ACGCACTCAT | GGTGTCGCGA |
| 841 | GTGCCCCTCT | CCCTACTCAT | TCTTGCTCAA | CTAATATTGG | CTTGACACCT | CTTGATGGAT |
| 901 | AACCACTGAA | TGGCAAATAA | ACGAATTC   | 3'.        |            |            |

3. The DNA molecule of claim 1, comprising the nucleotide sequence

| 1   | GAATTCCCGG | ACTACGAACA | ACCCATCGAG | AGAACAGTGG | TAGAATATCC | ATCACTACGT |
|-----|------------|------------|------------|------------|------------|------------|
| 61  | GACATCTTTG | CTTGGGAACC | TCCGACTTCT | AACTCCATTG | GCCTAACTTG | GCAAAGGCAT |
| 121 | GCATTTCCTG | GTGTGGAACG | TGAAGTGCTC | ACATTGAAGG | CAGTGCCGAC | TTCTGAACCC |
| 181 | AATAACACCA | AGACAGCATA | TGCAAAGCTC | GGCAGCGGAA | AAGTCACTCT | TGATGGACTG |
| 241 | AAGCCCAATG | CCACATATCT | TGTGACTGCG | ACGGCAAATA | TAAGTGGAGA | CACAATTCTG |
| 301 | GTATTGAGCA | ATACTTTTCA | TACACTGGCC | AATGGCACAA | ATATTATAAA | TAACATCTTC |
| 361 | CATTGGGGTC | CTGTGACTAA | TCAATCAATT | CAAGTAAGAT | GGGATCAGAT | AAAACCGGAG |
| 421 | GAAACAAGCG | CTCTGATAGT | CACACTGACG | GCAGAGATGG | CTTCTGACCC | CGGAGTGGAA |
| 481 | AGATCGGAGT | CTGCACTCTT | CGGTAAAGGA | AAGGTCACTG | TT.        |            |

4. The DNA molecule of claim 1, comprising the nucleotide sequence

| 1   | GAATTCCCGG | ACTACGAACA | ACCCATCGAG | AGAACAGTGG | TAGAATATCC | ATCACTACGT |
|-----|------------|------------|------------|------------|------------|------------|
| 61  | GACATCTTTG | CTTGGGAACC | TCCGACTTCT | AACTCCATTG | GCCTAACTTG | GCAAAGGCAT |

-continued

| | | | | | |
|---|---|---|---|---|---|
| 121 GCATTTCCTG | GTGTGGAACG | TGAAGTGCTC | ACATTGAAGG | CAGTGCCGAC | TTCTGAACCC |
| 181 AATAACACCA | AGACAGCATA | TGCAAAGCTC | GGCAGCGGAA | AAGTCACTCT | TGATGGACTG |
| 241 AAGCCCAATG | CCACATATCT | TGTGACTGCG | ACGGCAAATA | TAAGTGGAGA | CACAATTCTG |
| 301 GTATTGAGCA | ATACTTTTCA | TACACTGGCC | AATGGCACAA | ATATTATAAA | TAACATCTTC |
| 361 CATTGGGGTC | CTGTGACTAA | TCAATCAATT | CAAGTAAGAT | GGGATCAGAT | AAAACCGGAG |
| 421 GAAACAAGCG | CTCTGATAGT | CACACTGACG | GCAGAGATGG | CTTCTGACCC | CGGAGTGGAA |
| 481 AGATCGGAGT | CTGCACTCTT | CGGTAAAGGA | AAGGTCACTG | TTGACGGACT | GGAGTCCGAC |
| 541 ACACTATATA | TTGCGACTGT | GATGGTATTT | AGAAATGGAA | GGCAATACTT | CAATTCCACC |
| 601 AGAGATATTC | GAACACTCAA | ATCTGGCCAT | AAGGAGGTAA | CAGTCGTAAC | AACTAGT. |

5. A recombinant expression vector comprising a DNA molecule as claimed in claim 1.

6. A recombinant expression vector comprising a DNA molecule as claimed in claim 2.

7. A recombinant expression vector comprising a DNA molecule as claimed in claim 3.

8. A recombinant expression vector comprising a DNA molecule as claimed in claim 4.

9. A vector as claimed in claim 5 which is pSj10, Bam7Stop7-45W.

10. A vector as claimed in claim 5 which is pGEX-1-45W.

11. A vector as claimed in claim 5 which is pGEX-2-45W.

12. A host cell transformed with a vector as claimed in claim 5 and capable of expressing the T.ovis polypeptide or fragment thereof which is encoded.

13. The host cell of claim 12 which is a prokaryote.

14. The host cell of claim 13, wherein the prokaryote host is E.coli.

15. The E.coli host cell as claimed in claim 14 selected from the group consisting of strain JM101 and JM109.

16. The host cell of claim 12 which is a eukaryote.

17. The host cell of claim 16, wherein said eukaryote is a mammalian cell, a yeast cell or an insect cell.

18. A method of producing a polypeptide of T.ovis or a fragment thereof which comprises the steps of:

culturing a host cell according to claim 12; and recovering the polypeptide or fragment thereof encoded by the DNA molecule contained in said host cell.

19. AN isolated or purified antibody which specifically binds to a T. ovis polypeptide running as a 47–52 kDa doublet on SDS-PAGE and which comprises the amino acid sequence of FIG. 2, or to a fragment of said polypeptide which reduces the severity of T. ovis infection in a ruminant, said antibody also binding to a protective antigen of a cestode parasite other than T. ovis.

* * * * *